(12) United States Patent
Lee et al.

(10) Patent No.: US 7,091,326 B2
(45) Date of Patent: Aug. 15, 2006

(54) FUSION PROTEIN HAVING ENHANCED IN VIVO ERYTHROPOIETIN ACTIVITY

(75) Inventors: Dong-eok Lee, Seoul (KR); Myung-suk Oh, Yicheon (KR); Ki-wan Kim, Seoul (KR); Bo-sup Chung, Anyang (KR); Ji-sook Park, Seoul (KR)

(73) Assignee: Cheil Jedang Corporation, Seoul (KR)

( * ) Notice: Subject to any disclaimer, the term of this patent is extended or adjusted under 35 U.S.C. 154(b) by 405 days.

(21) Appl. No.: 10/196,183

(22) Filed: Jul. 17, 2002

(65) Prior Publication Data

US 2003/0113871 A1 Jun. 19, 2003

(30) Foreign Application Priority Data

Dec. 3, 2001 (KR) ............................. 2001-75994

(51) Int. Cl.
*C07K 14/59* (2006.01)
*C07K 14/505* (2006.01)
*C12N 15/00* (2006.01)
*C12N 15/62* (2006.01)

(52) U.S. Cl. .................. 530/397; 530/399; 435/69.1

(58) Field of Classification Search ............... 530/350, 530/397, 398, 399; 435/69.1, 325, 320.1; 536/23.1, 23.4
See application file for complete search history.

(56) References Cited

U.S. PATENT DOCUMENTS 5,712,122 A * 1/1998 Boime et al. ............... 435/69.7

FOREIGN PATENT DOCUMENTS

| EP | 0 640 619 A1 | 3/1995 |
|---|---|---|
| EP | 0640619 A1 | 3/1995 |
| JP | 8-506023 | 7/1996 |
| JP | 11-155584 | 6/1999 |
| JP | 2001-064300 | 3/2001 |
| WO | WO 95/05465 | 2/1995 |
| WO | WO 01/03737 | 1/2001 |
| WO | WO 01/36489 A2 | 5/2001 |
| WO | WO 01/36489 A3 | 5/2001 |
| WO | WO 02/48194 | 6/2002 |
| WO | WO 02/48194 A1 | 6/2002 |

OTHER PUBLICATIONS

Wells, Additivity of Mutational Effects in Proteins. Biochemistry 29:8509-8517 (1990).*
Furuhashi et al., "Fusing the Carboxy-Terminal Peptide of the Chorionic Gonadotropin (CG) β-Subunit to the Common α-Subunit: Retention of O-Linked Glycosylation and Enhanced *in Vivo* Bioactivity of Chimeric Human CG, Molecular Endocrinology", 9:1, 54-63 (1995).
Sytkowski et al., "An Erythropoietin Fusion Protein Comprised of Identical Repeating Domains Exhibits Enhanced Biological Properties", The Journal of Biological Chemistry, 274:35, 24773-24778, 1999.
Communication from Japanese Patent Office.

* cited by examiner

*Primary Examiner*—Brenda Brumback
*Assistant Examiner*—Regina M. DeBerry
(74) *Attorney, Agent, or Firm*—Leydig, Voit & Mayer, Ltd.

(57) ABSTRACT

Provided is a fusion protein comprising, at its carboxy terminal of human erythropoietin (EPO), a mutant having one to four amino acid substitutions in the carboxy terminal peptide (CTP) fragment of a human chorionic gonadotropin (HCG) β subunit, for increasing an in vivo half-life activity of EPO. The in vivo half-life can be greatly elongated while retaining the intrinsic activity of the EPO, without increasing the sugar chain content.

6 Claims, 5 Drawing Sheets

Fig. 1.

```
1                                              10
TCC GCT TCC GCG AAG GCC CCT CCC CCC GCC CTT CCA AGC CCA GCC
Ser Ser Ser Ala Lys Ala Pro Pro Pro Ala Leu Pro Ser Pro Ala
                    20                              27  28
CGA CTC CCG GGG CCC GCC GAC ACC CCG ATC CTC CCA CAA TAA
Arg Leu Pro Gly pro Ala Asp Thr Pro Ile Leu Pro Gln
```

Fig. 2.

```
ATG GGG GTG CAC GAA TGT CCT GCC TGG CTG TGG CTT CTC CTG TCC
MET Gly Val His Glu Cys Pro Ala Trp Leu Trp Leu Leu Leu Ser

CTG CTG TCG CTC CCT CTG GGC CTC CCA GTC CTG GGC GCC CCA CCA
Leu Leu Ser Leu Pro Leu Gly Leu Pro Val Leu Gly Ala Pro Pro

CGC CTC ATC TGT GAC AGC CGA GTC CTG GAG AGG TAC CTC TTG GAG
Arg Leu Ile Cys Asp Ser Arg Val Leu Glu Arg Tyr Leu Leu Glu

GCC AAG GAG GCC GAG AAT ATC ACG ACG GGC TGT GCT GAA CAC TGC
Ala Lys Glu Ala Glu Asn Ile Thr Thr Gly Cys Ala Glu His Cys

AGC TTG AAT GAG AAT ATC ACT GTC CCA GAC ACC AAA GTT AAT TTC
Ser Leu Asn Glu Asn Ile Thr Val Pro Asp Thr Lys Val Asn Phe

TAT GCC TGG AAG AGG ATG GAG GTC GGG CAG CAG GCC GTA GAA GTC
Tyr Ala Trp Lys Arg MET Glu Val Gly Gln Gln Ala Val Glu Val

TGG CAG GGC CTG GCC CTG CTG TCG GAA GCT GTC CTG CGG GGC CAG
Trp Gln Gly Leu Ala Leu Leu Ser Glu Ala Val Leu Arg Gly Gln

GCC CTG TTG GTC AAC TCT TCC CAG CCG TGG GAG CCC CTG CAG CTG
Ala Leu Leu Val Asn Ser Ser Gln Pro Trp Glu Pro Leu Gln Leu

CAT GTG GAT AAA GCC GTC AGT GGC CTT CGC AGC CTC ACC ACT CTG
His Val Asp Lys Ala Val Ser Gly Leu Arg Ser Leu Thr Thr Leu

CTT CGG GCT CTG GGA GCC CAG AAG GAA GCC ATC TCC CCT CCA GAT
Leu Arg Ala Leu Gly Ala Gln Lys Glu Ala Ile Ser Pro Pro Asp

GCG GCC TCA GCT GCT CCA CTC CGA ACA ATC ACT GCT GAC ACT TTC
Ala Ala Ser Ala Ala Pro Leu Arg Thr Ile Thr Ala Asp Thr Phe

CGC AAA CTC TTC CGA GTC TAC TCC AAT TTC CTC CGG GGA AAG CTG
Arg Lys Leu Phe Arg Val Tyr Ser Asn Phe Leu Arg Gly Lys Leu

AAG CTG TAC ACA GGG GAG GCC TGC AGG ACA GGG GAC TCC GCT TCC
Lys Leu Tyr Thr Gly Glu Ala Cys Arg Thr Gly Asp Ser Ala Ser

GCC AAG GCC CCT CCC CCC GCC CTT CCA AGC CCA GCC CGA CTC CCG
Ala Lys Ala Pro Pro Pro Ala Leu Pro Ser Pro Ala Arg Leu Pro

GGG CCC GCC GAC ACC CCG ATC CTC CCA CAA TAA
Gly pro Ala Asp Thr Pro Ile Leu Pro Gln
```

FUSION PROTEIN HAVING ENHANCED IN VIVO ERYTHROPOIETIN ACTIVITY

BACKGROUND OF THE INVENTION

1. Field of the Invention

The present invention relates to a fusion protein having an enhanced in vivo activity of an anti-pernicious anemia drug, erythropoietin (hereinafter, it is also referred to as "EPO"). More particularly, the present invention relates to a fusion protein having an enhanced EPO activity by increasing its in vivo half-life with its own amino acid sequences, that is, without increasing the glycosylation content, wherein the fusion protein contains an EPO molecule fused to a particular peptide naturally occurring in vivo.

2. Description of the Related Art

EPO is a glycoprotein having a molecular weight in the range of 30,000 to 34,000 Da, and is a hematopoietic factor promoting production and differentiation of red blood cells. The glycoprotein binds to a receptor of precursor cells of red blood cells to initiate its hematopoietic activity and causes an increase in the amounts of intracellular calcium ions, an enhancement of DNA biosynthesis and stimulation of hemoglobin formation. Also, recombinant human EPO(rhEPO) has been approved for the treatment of anemia associated with kidney failure, prematurity, hypothyroidism, malnutrition and so forth, and clinical use of rhEPO is continuously increasing. However, extensive use of rhEPO could be limited by inconvenience and high costs because rhEPO should be administered about three times a week due to its short half-life. Thus, the frequency of rhEPO administration for treatment could be reduced by maintaining an in vivo activity of EPO for a longer time.

In vivo biological activity of EPO is proportional to its in vivo half-life which has been known to be related with the content of sialic acid located at the terminus of sugar chains in EPO. Thus, the in vivo biological activity of EPO is greatly dependent upon the presence or absence of sugar chains. The types of sugar chains vary depending on cell types. Thus, when the same glycoprotein is expressed in different cells, the types of sugar chains of the protein are characteristically different depending on the cell types. It is known that bacterial cells, for example, *E. coli* could not attach sugar chains to its proteins. Since it is known that proteins expressed in *E. coli* do not have any sugar chains, EPO expressed in *E. coli* does not contain sugar chains. In this case, EPO is confirmed to be biologically active in vitro but not active at all in vivo. This is because EPO without sugar chains is more rapidly removed from the body, compared to EPO with sugar chains, resulting in an extremely short half-life. Consequently, the presence or absence of sugar chains in EPO plays an important role in the biological activity of EPO.

To date, a lot of researches have been vigorously carried out to increase the biological activity of EPO. Most of these researches focus on substitution of some amino acids by inducing mutation of EPO genes using mutagenesis techniques. For example, PCT/US94/09257 entitled "Erythropoietin Analogs", filed by Amgen Inc., disclosed a method of increasing an in vivo half-life by increasing the sugar chain content in EPO through mutagenesis. Increasing an in vivo half-life through EPO dimer formation has been also attempted (A. J. Sytkowski et al., J.B.C. vol. 274, No. 35, pp 24773–24778). Other methods for increasing the in vivo biological activity of EPO include fusing a novel amino acid, peptide or protein fragment to EPO molecules using genetic engineering, and to increase the sugar chain content in EPO, specifically the amounts of sialic acids. However, the kinds of amino acids, peptides or protein fragments used in this method are very limited. In most cases, such genetic modifications may result in a decrease or loss in specific activity of protein or cause antigenicity problems frequently occurring when those substances are used in vivo.

Researches into fusion proteins or chimeric proteins, rather than EPO, have been carried out, and one of the examples thereof is a follicle stimulating hormone, which is a sex hormone (Furuhashi et al., 1995, Mol. Endocrinol). However, such proteins have not yet been applied in the field because genetically modified proteins using genetic engineering pose several problems. It is not easy to obtain a modified target protein itself, requiring highly professional skills. Also, in most cases, the activities of proteins may be undesirably decreased or removed by addition of or substitution by new amino acids.

Under the circumstances, the present inventors began extensive studies into the development of a new method of increasing the in vivo activity of EPO by fusing new amino acids, peptides or proteins to EPO molecules. In the course of carrying out these studies, it was found that a fusion protein obtained by fusing carboxy terminal peptide (hereinafter, it is also referred to as "CTP") fragments of the β subunit of a human chorionic gonadotropin (hereinafter, it is also referred to as "HCG") which is a protein naturally occurring in vivo, to EPO, dramatically increases the in vivo half-life of the EPO. Also, the EPO contains amino acids having the function of increasing glycosylation sites while retaining the intrinsic activity of the EPO (see Korean Patent Application No. 10-2000-0075230).

SUMMARY OF THE INVENTION

The present inventors have unexpectedly discovered that CTP variants whose glycosylation site in the peptide had been removed also remarkably increased the in vivo half-life of EPO. As a result of this finding, CTP variants which can increase the in vivo stability of EPO through use of amino acid sequences, without increasing the content of sugar chains in EPO, have been developed, leading the present inventors to complete the present invention.

The present invention, in which CTP variants whose glycosylation sites have been removed are used, is distinguishable from the prior art, in which an in vivo half-life is increased by increasing the content of the sugar chains in EPO, and is based on the discovery of CTP variants capable of increasing the in vivo stability of EPO.

Accordingly, it is an objective of the present invention to provide a fusion protein having an enhanced in vivo activity of human EPO, wherein the fusion protein includes an EPO molecule fused to a CTP variant of a HCG β subunit at its carboxy terminus.

It is another objective of the present invention to provide a nucleic acid that encodes the fusion protein, a recombinant vector containing the nucleic acid, and a cell line transfected with the recombinant plasmid.

It is still another objective of the present invention to provide a method for preparing a fusion protein having an enhanced human EPO activity by culturing the transformed cell line.

In one embodiment of the present invention, there is provided a fusion protein having an enhanced in vivo activity of human EPO, wherein the fusion protein includes an EPO molecule fused to a CTP variant of a HCG β subunit (hereinafter, it is also referred to as "ATP") at its carboxy terminus. Preferably, the CTP includes all or some of the amino acids corresponding to positions 112–145, preferably to positions 118–145, of the HCG β subunit, the amino acids being described by SEQ ID No. 1.

ATP, which is a CTP variant, has the function of increasing the half-life of the EPO molecule with its own amino acid sequences, i.e, without increasing the sugar chain content of EPO.

Thus, unless the action of a target fusion protein increasing an in vivo EPO activity is adversely affected, positions and kinds of amino acids experiencing a change in position within the above-noted range are not specifically restricted. In other words, as long as the fusion protein maintains the activity of increasing an in vivo EPO activity, amino acids at positions belonging to the above-noted range can be replaced at any position, with any amino acids.

For example, it is preferable that ATP has one or more amino acids substitutions at positions 121, 127, 132 and 138, and most preferably has serine (Ser) residues at positions 121, 127, 132 and 138 replaced with alanine (Ala) residues (FIG. 1. SEQ ID NO. 11). In this case, the fusion protein according to the present invention has the amino acid sequence described by SEQ ID NO. 2. From the finding that Ser residues at the above positions can be replaced with Ala residues, it is clear to one skilled in the art that any other amino acid having similar size and charge as Ala, for example, glycine (Gly), can replace Ser.

In another embodiment of the present invention, there is provided a nucleic acid that encodes the fusion protein, a recombinant vector containing the nucleic acid, and a cell line transfected with the recombinant plasmid, preferably a Chinese hamster ovary (CHO) cell.

In still another embodiment of the present invention, there is provided a method for preparing a fusion protein having an enhanced human EPO activity by culturing the transformed cell line.

BRIEF DESCRIPTION OF THE DRAWINGS

The above objects and advantages of the present invention will become more apparent by describing in detail preferred embodiments thereof with reference to the attached drawings in which:

FIG. 1 depicts the base (SEQ ID NO. 13) and amino acid (SEQ ID NO. 11) sequences of ATP as a CTP variant;

FIG. 2 depicts the base (SEQ ID NO. 12) and amino acid (SEQ ID NO. 2) sequences of a fusion protein (EATP) of EPO and ATP;.

DETAILED DESCRIPTION OF THE INVENTION

The present invention will now be described in more detail. The present invention is processed by steps of acquisition and cloning of genes of a target fusion protein, construction of expression vectors of a target gene, transfection of animal cells and EATP expression, and purification of the expressed EATP and activity measurement.

(1) Acquisition of Genes

Complementary DNA (cDNA) of EPO can be acquired by employing a conventional reverse transcription-polymerase chain reaction (RT-PCR) technique using a RT-PCT Premix Kit available from Bioneer Corp., Korea, in which primers EP1 and EC2 complementary to both terminals of EPO cDNA previously prepared from a cDNA library of the human embryonic liver (available from Invitrogen Corp.) are used.

```
EP1:  ATGGGGGCACGAATGTCCTGCCTGGCTGG    (SEQ ID NO:3)

EC2:  GTCCCCTGTCCTGCAGGCCT             (SEQ ID NO:4)
```

EPO cDNA is cloned into a cloning vector pGEM-T (Promega Corp.), which is termed pGEMT-EPO, and its base sequence is identified for use as template in subsequent operations.

CTP variant genes of a HCG β subunit used in the present invention are obtained by artificial synthesis and self-priming PCR. The synthesized gene fragments are EA1, A2, A3 and A4:

```
                                                   (SEQ ID NO:5)
EA1:   AGGGGAGGCCTGCAGGACAGGGGACTCCTCTTCCG (SEQ ID NO:6)
A2:    GGAAGGGC GGGGGGAGGGGCCTTG GC GGAAGAGGA (SEQ ID NO:7)
A3:    CCGC CCTTCCAAGCCCAG CCCGACTCCCGGGGCCC (SEQ ID NO:8)
A4:    TTATTGTGGGAGGATCGGGGTGTCG GC GGGCCCCG
```

(Bold Portions Indicate Portions for Amino Acid Replacement.)

Each 1 μL of four genes is taken (50 pmole/μL) to be subjected to PCR using a high fidelity Taq system (Boehringer Manheim Corp.).

Gene fragments (Modified CTP genes) of approximately 100 bps in size are identified in a 1% Agarose gel. These genes encode a peptide obtained by replacing 4 Ser residues at positions 121, 127, 132 and 138 among 28 carboxy terminal amino acids at positions 118–145 of a HCG β subunit, with Ala residues (see FIG. 1. SEQ ID NO. 11).

Gene fragments (Modified CTP genes) of approximately 100 bps in size are identified in a 1% Agarose gel. These genes encode a peptide obtained by replacing 4 Ser residues at positions 121, 127, 132 and 138 among 28 carboxy terminal amino acids at positions 118–145 of a HCG β subunit, with Ala residues (see FIG. 1).

PCR is performed using a pGEMT-EPO as template and EP1 and EC2 as primers, yielding only EPO genes. Then, PCR is further performed using both the EPO genes and the modified CTP genes as templates and using EP11 and EP22 primers by means of the high fidelity Taq system, thereby acquiring a desired fusion protein with gene fragments of approximately 630 bps (to be termed EATP genes).

```
EP11:  TAAGCTTATGGGGGTGCACGAATGT        (SEQ ID NO:9)

EP22:  TGGATCCTTATTGTGGGAGGATCGGGGT    (SEQ ID NO:10)
```

Figure 3:
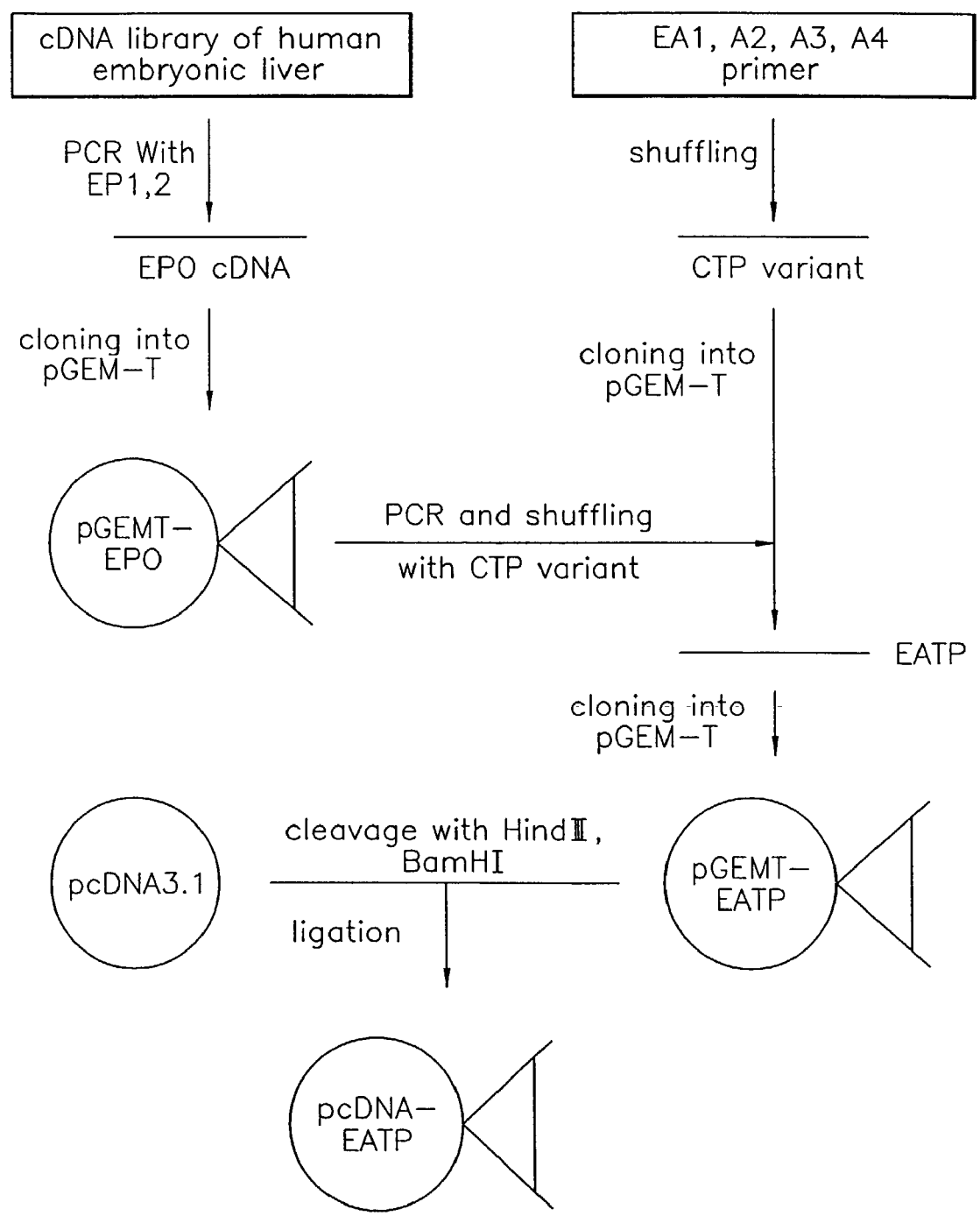
FIG. 3 is a graphic representation illustrating production of an expression vector pcDNA3.1-EATP.

These genes are cloned into pGEM-T cloning vectors and then base sequences are identified (to be termed pGEMT-EATP) (see FIG. 3).

(2) Construction of Expression Vectors pcDNA3.1 vector (Invitrogen Corp.) is used as an expression vector. Both termini of the EATP gene in PGEMT-EATP have Hind III and BamH I restriction enzyme sites derived from the primers EP11 and EP22. pcDNA3.1 and the obtained pGEMT-EATP are treated with Hind III and BamH I. The linearized pcDNA3.1 and EATP gene are obtained from an Agarose gel using a Qiagen elution kit, followed by ligation, thereby transforming *E. coli* NM522. Plasmids are isolated from colonies resulting after incubation overnight in an LB-Ampicillin solid medium, and are treated with the restriction enzymes Hind III and BamH I. Then, only colonies inserted EATP are selected by 1% Agarose gel electrophoresis. The resultant plasmids are termed pcDNA3.1-EATP (see FIG. 3).

(3) Transfection of CHO Cells and EATP Expression

CHO cells (DG44) are grown in a 60 mm dish to prepare 40–80% confluent cells ($1-4 \times 10^5$ cells/60 mm dish). 3 μL of a superfection reagent (Boehringer Manheim Corp.) and 97 μL of media (α-MEM with media, serum free and non-antibiotic) are mixed sufficiently, and approximately 2 μg of a plasmid pcDNA3.1-EATP DNA (more than 0.1 μg/μL) and 0.2 μg of a dihydrofolate reductase (dhfr) gene containing vector pLTRdhfr26 (ATCC37295) are added to the resultant mixture and reacted at room temperature for 5–10 minutes to then be added to the cells. After one day, the media are replaced with α-MEM without media (containing 500 μg/mL G418) with 10% FBS. The cells are replenished with media with 500 μg/mL G418 and cultured for 7–10 days. Then, cells without G418-resistant genes and cells of negative control group all die. After cells selected from the G418 media are sufficiently cultured, an EATP protein expressed from the media is confirmed using an EPO ELISA kit (Boehringer Manheim Corp.).

(4) Purification of Expressed EATP

Using an anti-EPO monoclonal antibody (R&D Inc.), affinity resins for purification are prepared as follows.

0.3 g of CNBr-activated Sepharose 4B is swollen in 1 mM HCl for 20 minutes and loaded onto a column, followed by washing with 1 mM HCl. Then, the resultant resin is further washed in 4 mL coupling buffer solution (0.1 M $NaHCO_3$ and 0.5 M NaCl, pH 8.3) transferred to a tube and immediately mixed with anti-EPO monoclonal antibody in the coupling buffer solution (500 μg/vial), and then reacted at room temperature for 2 hours. At this time, the tube is sufficiently shaken. Then, the resultant product is replaced with a blocking buffer (0.2 M glycine, pH 8.0) and reacted at room temperature for 2 hours with agitation. The resultant resin is washed sequentially with a 6.5 mL coupling buffer solution, a 6.5 mL acetate buffer solution (0.1 M acetic acid, 0.5 M NaCl, pH 4) and a 6.5 mL coupling buffer solution. The prepared resin is packed into a column and then subjected to purification as follows.

Figure 4:
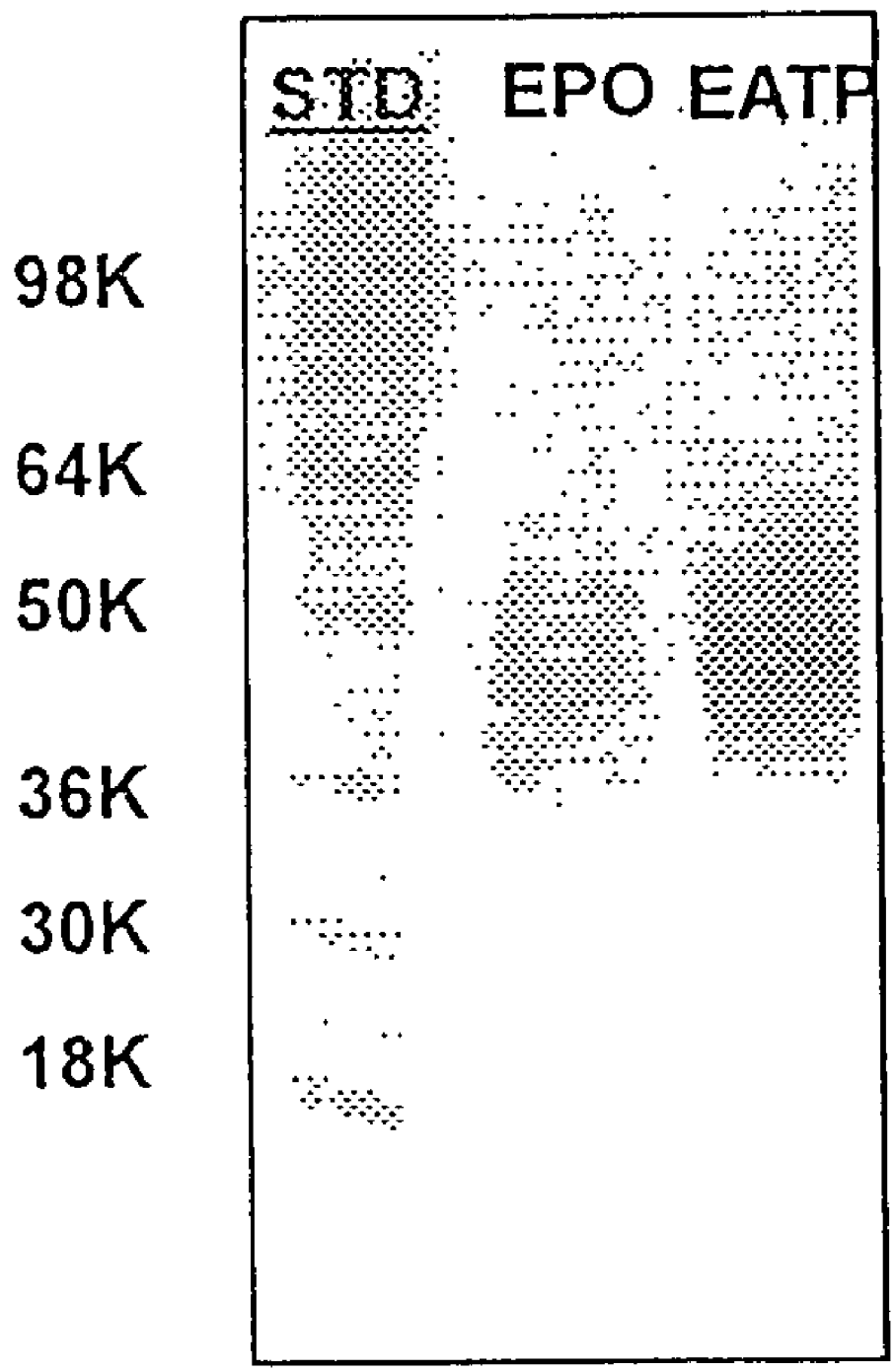
FIG. 4 is an electrophoresis photograph of purified EATP.

Cells are grown in a serum-free medium for one day and then only the medium is concentrated approximately 5 times using a ultrafiltration filter, for example, Centriprep (having a nominal molecular weight cutoff of 10,000) (Millipore Corp.). Then, the concentrated solutions are loaded onto a column equilibrated with phosphate buffered saline (PBS) at a flow rate about 20 mL/hr and washed again with PBS. The target proteins are eluted in an elution buffer solution (0.1 M glycine, pH 2.8) and then immediately titrated with 1 M Tris solution for adjustment to pH 7.5. The purity of the purified EATP is 97% or higher as verified by SDS-PAGE and silver staining (see FIG. 4).

(5) Activity Measurement by Bioassay Test and Biochemical Analysis

Biological activities of the expressed and appropriately purified EPO and EATP are measured by a bioassay using spleen cells of a mouse treated with phenylhydrazine. The result shows that the activity of EATP is higher than that of EPO, suggesting that the presence of added carboxy terminals in EATP does not inhibit the activity of EPO.

(6) Pharmacokinetic Test

In order to confirm whether the prepared candidate materials actually have a longer in vivo half-life, pharmacokinetic tests are performed on mice. Here, the candidate materials are intravenously administered to four mice at dosages of 20 units for each mouse. To evaluate the concentration profile in blood, blood is gathered from the mice and the concentration in the gathered blood is measured using an EIA kit (Boehringer Manheim Corp.). The pharmacokinetic test performed on mice shows that candidate material EATP has a much longer half-life than the control material EPO (see FIG. 5).

The present invention is further illustrated in the following examples, which should not be misconstrued as limiting the scope of the invention.

EXAMPLE 1

Acquisition of Genes cDNA of EPO was acquired by employing a conventional RT-PCR technique using a RT-PCT Premix Kit (Bioneer Corp., Korea), in which primers EP1 and EC2 complementary to both terminals of EPO cDNA previously prepared from a cDNA library of the human embryonic liver (Invitrogen Corp.) were used. 30 cycles of PCR reactions were performed in the conditions of 35 seconds at 55° C. (annealing), 40 seconds at 72° C., and 20 seconds at 94° C., yielding EPO cDNA. The obtained EPO cDNA was cloned into a cloning vector PGEM-T (Promega Corp.). In other words, the product of PCR was eluted from 1% Agarose, ligated to pGEM-T, followed by transformation of *E. coli* NM522. After overnight incubation in an X-gal/IPTG smeared LB-Ampicillin solid medium, plasmid DNA was isolated from white colonies and reacted with restriction enzymes Sac I and Sac II to select colonies having EPO cDNA inserts therein. The obtained vector was termed pGEMT-EPO and its base sequence was identified for use as a template in subsequent processes.

Modified CTP genes of a HCG β subunit were obtained by artificial synthesis and self-priming PCR. The synthesized gene fragments were EA1, A2, A3 and A4.

Each 1 μL of four genes was taken (50 pmole/μL) to be subjected to 15 cycles of PCR using a high fidelity Taq system (Boehringer Manheim Corp.) under conditions of 40 seconds at 55° C. (annealing), 40 seconds at 72° C. and 20 seconds at 94° C. Gene fragments of approximately 100 bps in size were identified in a 1% Agarose gel (modified CTP genes).

These genes encode a peptide obtained by replacing 4 Ser residues at positions 121, 127, 132 and 138 among 28 carboxy terminal amino acids of a HCG β subunit, with Ala residues (FIG. 1. SEQ ID NO. 11).

PCR was performed using a pGEMT-EPO template and EP1 and EC2 primers, yielding only EPO genes. Then, 30 cycles of PCR were further performed using both the EPO genes and the modified CTP genes obtained as templates and using EP11 and EP22 primers by means of the high fidelity Taq system under conditions of 42 seconds at 57° C. (annealing), 60 seconds at 72° C., and 20 seconds at 94° C. Thus, approximately 630 bps of fused gene fragments were obtained (to be termed EATP genes). These genes were cloned into PGEM-T using above mentioned method (to be termed pGEMT-EATP), and its sequences were identified.

EXAMPLE 2

Construction of Expression Vector pcDNA3.1-EATP pcDNA3.1 vector (Invitrogen) was used as expression vector. Both terminus of the EATP gene in pGEMT-EATP have Hind III and BamH I restriction sites derived from the primers EP11 and EP22.

pcDNA3.1 and the obtained pGEMT-EATP were treated with the restriction enzymes Hind III and BamH I. The linearized pcDNA3.1 and EATP gene were obtained from an Agarose gel using a Qiagen elution kit, followed by ligation, thereby transforming E. coli NM522. Plasmids were isolated from colonies resulting after incubating overnight in an LB-Ampicillin solid medium, and were treated with the restriction enzymes Hind III and BamH I. Then, only colonies inserted EATP were selected by 1% Agarose gel electrophoresis. The resultant plasmids were termed pcDNA3.1-EATP (see FIG. 3).

EXAMPLE 3

Transfection of CHO Cells and EATP Expression

CHO cells (DG44) were grown in a 60 mm dish to prepare 40–80% confluent cells ($1-4 \times 10^5$ cells/60 mm dish). 3 μL of a superfection reagent (Boehringer Manheim Corp.) and 97 μL of media (α-MEM with media, serum-free and non-antibiotic) were mixed sufficiently, and approximately 2 μg of a plasmid pcDNA3.1-EATP DNA (more than 0.1 μg/μL) and 0.2 g of a dihydrofolate reductase (dhfr) gene containing vector pLTRdhfr26 (ATCC37295) were added to the resultant mixture and reacted at room temperature for 5–10 minutes and then added to the cells. After one day elapsed, the media were replaced with α-MEM without media (containing 500 μg/mL G418) with 10% FBS. The cells were replenished with media containing 500 μg/mL G418, and cultured for 7–10 days. Then, cells without G418-resistant genes and cells of negative control group all died. After cells selected from the G418 media were sufficiently cultured, EATP protein expressed from the media was confirmed using an EPO ELISA kit (Boehringer Manheim Corp.).

EXAMPLE 4

Purification of Expressed EATP

Using an anti-EPO monoclonal antibody (R&D Inc.), affinity resins for purification were prepared as follows.

0.3 g of CNBr-activated Sepharose 4B was swollen in 1 mM HCl for 20 minutes and loaded onto a column, followed by washing with 1 mM HCl. Then, the resultant resin was further washed in 4 mL coupling buffer solution (0.1 M NaHCO$_3$ and 0.5 M NaCl, pH 8.3), transferred to a tube and immediately mixed with anti-EPO monoclonal antibody in the coupling buffer solution (500 μg/vial), and then reacted at room temperature for 2 hours with agitation. At this time, the tube was sufficiently shaken. Then, the resultant product was replaced with a blocking buffer (0.1 M glycine, pH 8.0) and reacted at room temperature for 2 hours. The resultant product was washed sequentially with a 6.5 mL coupling buffer solution, a 6.5 mL acetate buffer solution (0.1 M acetic acid, 0.5 M NaCl, pH 4) and a 6.5 mL coupling buffer solution. The prepared resin was packed into a column and then subjected to purification as follows.

Cells were grown in a serum-free medium for one day and then only the medium was concentrated approximately 5 times using a ultrafiltration filter of Centriprep (having a nominal molecular weight cutoff of 10,000) (Millipore Corp.). Then, the concentrated solutions were loaded onto a column equilibrated with PBS at a flow rate about 20 mL/hr and washed again with PBS. The target proteins were eluted in an elution buffer solution (0.1 M glycine, pH 2.8) and then immediately titrated with 1 M Tris solution for adjustment to pH 7.5. The purity of the purified EATP was 97% or higher as verified by SDS-PAGE and silver staining (see FIG. 4).

EXAMPLE 5

Activity Measurement by Bioassay Test

Phenylhydrazine was administered to a mouse once a day for 2 days at the dose of 60 mg/kg. After 3 days, an enlarged spleen was isolated from the mouse and pulverized with a homogenizer to gain spleen cells. The spleen cells were diluted to a concentration of $6 \times 10^6$ cells/mL and each 100 μL of the diluted sample was transferred to a 96-well plate. Standard EPO (0–500 mU/mL) and the expressed EPO and EATP (each 100 mU/mL) were added to the respective wells. Then, the plate was stored in a CO$_2$ incubator maintained at 37° C. for 22 hours. 50 μL of dimethyl-$^3$H-thymidine (20 μCi/mL) was added to each well. The resultant plate was further reacted for 2 hours, and then the sample solutions of each well were adsorbed to a glass filter (Nunc 1-73164). The filter was washed three times with saline and the radioactivity of the filter was measured using a beta (β) counter. The measurements showed that the activity of EATP was substantially equal to or slightly higher than that of EPO, suggesting that the presence of added carboxy terminals in EATP does not inhibit the activity of EPO.

EXAMPLE 6

Pharmacokinetic Test

Figure 5:
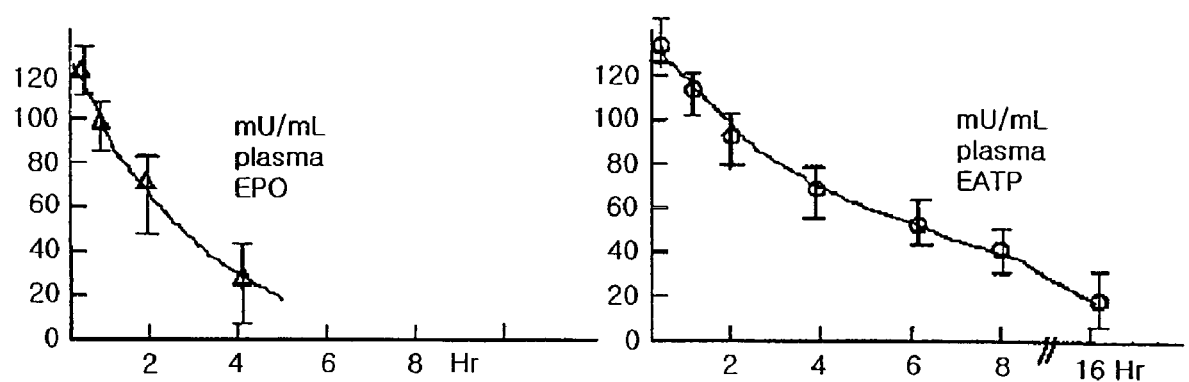
FIG. 5 graphically represents pharmacokinetic analysis results of EATP and EPO.

In order to confirm whether the prepared candidate materials actually have a longer in vivo half-life, pharmacokinetic tests were performed on mice. Here, the fusion protein purified by the method described in Example 5 was intravenously administered to four mice at dosages of 20 units for each mouse. To evaluate the concentration profile in blood, blood was gathered from the mice at regular time intervals, that is, every 30 minutes at the beginning and every 2 hours after 2 hours. and the concentration in the gathered blood was determined using an EIA kit (Boehringer Manheim.). The result of the pharmacokinetic test is shown in FIG. 5. As shown in FIG. 5, the candidate material EATP had a much longer (more than 2.5 times longer) half-life than the control material EPO.

According to the present invention, the in vivo activity of EPO can be enhanced by increasing the in vivo half-life while retaining the intrinsic activity of the EPO with its own amino acid, i.e., without increasing the sugar chain content of EPO.

What is claimed is:

1. A fusion protein comprising human erythropoietin (EPO) having a carboxy terminal and a mutant linked to the carboxy terminal, said mutant being the carboxy terminal peptide (CTP) fragment of a human chorionic gonadotropin (HCG) β subunit having serine residues at positions 121, 127, 132, and 138 of the HCG β subunit replaced with alanine, wherein the CTP fragment has 34 amino acids corresponding to amino acid positions 112–145 of the HCG β subunit or 28 amino acids corresponding to amino acid positions 118–145 of the HCG β subunit.

2. The fusion protein according to claim 1, wherein the CTP fragment has the amino acid sequence set forth in SEQ ID NO. 11.

3. A nucleic acid encoding the fusion protein as claimed in claim 1.

4. The nucleic acid according to claim 3, the nucleic acid having the nucleotide sequence set forth in SEQ ID NO. 12.

5. A method for preparing a fusion protein having an enhanced in vivo EPO activity comprising culturing a cell line transfected with a recombinant vector containing the nucleic acid as claimed in claim 3.

6. A method for preparing a fusion protein having an enhanced in vivo EPO activity comprising culturing a cell line transfected with a recombinant vector containing the nucleic acid as claimed in claim 4.

* * * * *

SEQUENCE LISTING

<160> NUMBER OF SEQ ID NOS: 10

<210> SEQ ID NO 1
<211> LENGTH: 34
<212> TYPE: PRT
<213> ORGANISM: Homo sapiens
<220> FEATURE:
<221> NAME/KEY: Peptide
<222> LOCATION: (1)..(34)
<223> OTHER INFORMATION: Amino acids in the positions of 112 to 145 of
      human chorionic gonadotropin(HCG) beta submit

<400> SEQUENCE: 1

Asp Pro Arg Phe Gln Asp Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

Pro Gln

<210> SEQ ID NO 2
<211> LENGTH: 220
<212> TYPE: PRT
<213> ORGANISM: Artificial Sequence
<220> FEATURE:
<223> OTHER INFORMATION: Fusion prfotein (EATP) of erythropoietin (EPO)
      and a variant of carboxy terminal peptide (ATP) of human chorionic
      gonadotropin (HCG) beta subunit

<400> SEQUENCE: 2

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Ser Ser Ser Ala Lys Ala Pro Pro Ala Leu Pro Ser Pro Ala Arg
        195                 200                 205

Leu Pro Gly Pro Ala Asp Thr Pro Ile Leu Pro Gln
    210                 215                 220

```
<210> SEQ ID NO 3
<211> LENGTH: 29
<212> TYPE: DNA
<213> ORGANISM: Artificial Sequence
<220> FEATURE:
<223> OTHER INFORMATION: Primer EP1 having the nucleotide sequence
      complementary to the terminal sequence of EPO cDNA

<400> SEQUENCE: 3
atgggggcac gaatgtcctg cctggctgg                                            29

<210> SEQ ID NO 4
<211> LENGTH: 20
<212> TYPE: DNA
<213> ORGANISM: Artificial Sequence
<220> FEATURE:
<223> OTHER INFORMATION: Primer EC2 having the nucleotide sequence
      complementary to the terminal sequence of EPO cDNA

<400> SEQUENCE: 4 gtccctgtc ctgcaggcct                                                       20

<210> SEQ ID NO 5
<211> LENGTH: 35
<212> TYPE: DNA
<213> ORGANISM: Artificial Sequence
<220> FEATURE:
<223> OTHER INFORMATION: variant of HCG beta subunit CTP gene fragment
      EA1

<400> SEQUENCE: 5
aggggaggcc tgcaggacag gggactcctc ttccg                                     35

<210> SEQ ID NO 6
<211> LENGTH: 35
<212> TYPE: DNA
<213> ORGANISM: Artificial Sequence
<220> FEATURE:
<223> OTHER INFORMATION: Variant of HCG beta subunit CTP gene fragment
      A2

<400> SEQUENCE: 6
ggaagggcgg ggggaggggc cttggcggaa gagga                                     35

<210> SEQ ID NO 7
<211> LENGTH: 34
<212> TYPE: DNA
<213> ORGANISM: Artificial Sequence
<220> FEATURE:
<223> OTHER INFORMATION: Variant of Hcg beta subunit CTP ene fragment A2

<400> SEQUENCE: 7
ccgcccttca agcccagccc gactcccggg gccc                                      34

<210> SEQ ID NO 8
<211> LENGTH: 35
<212> TYPE: DNA
<213> ORGANISM: Artificial Sequence
<220> FEATURE:
<223> OTHER INFORMATION: Variant of HCG beta subunit CTP gene fragment
      A4

<400> SEQUENCE: 8
ttattgtggg aggatcgggg tgtcggcggg ccccg                                     35

<210> SEQ ID NO 9
```

```
<211> LENGTH: 25
<212> TYPE: DNA
<213> ORGANISM: Artificial Sequence
<220> FEATURE:
<223> OTHER INFORMATION: Primer EP11 for PCR to obtain the desired
      fusion gene EATP

<400> SEQUENCE: 9
taagcttatg ggggtgcacg aatgt                                         25

<210> SEQ ID NO 10
<211> LENGTH: 28
<212> TYPE: DNA
<213> ORGANISM: Artificial Sequence
<220> FEATURE:
<223> OTHER INFORMATION: Primer EP22 for PCR to obtain the desired
      fusion gene EATP

<400> SEQUENCE: 10
tggatcctta ttgtgggagg atcggggt                                      28
```